United States Patent
Xi et al.

(10) Patent No.: US 6,960,693 B2
(45) Date of Patent: Nov. 1, 2005

(54) OXIDATION REACTION PROCESS CATALYZED BY PHASE-TRANSFER CATALYST CONTROLLING REACTION

(75) Inventors: Zuwei Xi, Liaoning (CN); Yu Sun, Liaoning (CN); Kunlan Li, Liaoning (CN); Ning Zhou, Liaoning (CN)

(73) Assignees: China Petroleum & Chemical Corporation, Beijing (CN); Dalian Institute of Chemical Physics the Chinese Academy of Sciences, Liaoning (CN)

(*) Notice: Subject to any disclaimer, the term of this patent is extended or adjusted under 35 U.S.C. 154(b) by 57 days.

(21) Appl. No.: 10/432,874

(22) PCT Filed: Nov. 29, 2001

(86) PCT No.: PCT/CN01/01589
§ 371 (c)(1),
(2), (4) Date: May 28, 2003

(87) PCT Pub. No.: WO02/44110
PCT Pub. Date: Jun. 6, 2002

(65) Prior Publication Data
US 2004/0030054 A1 Feb. 12, 2004

(30) Foreign Application Priority Data
Nov. 29, 2000 (CN) .................................. 00 1 23339 A
Aug. 27, 2001 (CN) .................................. 01 1 23652 A
Aug. 27, 2001 (CN) .................................. 01 1 23653 A

(51) Int. Cl.$^7$ .................... C07C 321/00; C07C 45/00; C07C 35/08; C07D 313/00; C07F 15/00
(52) U.S. Cl. ........................ 568/22; 568/25; 568/402; 568/836; 568/910; 549/266; 549/272; 549/512; 549/523; 549/529; 549/531; 556/14; 556/20
(58) Field of Search .................... 568/22, 25, 402, 568/836, 910; 549/266, 272, 512, 523, 529, 531; 556/14, 20

(56) References Cited
U.S. PATENT DOCUMENTS 3,350,422 A * 10/1967 Kollar ..................... 260/348.5
3,887,490 A * 6/1975 Schreyer et al. ............ 252/414
4,008,133 A * 2/1977 Gelbin et al. ................. 204/80
4,562,276 A * 12/1985 Venturello et al. ............ 556/20
5,324,849 A * 6/1994 Bonsignore et al. .......... 556/14

OTHER PUBLICATIONS

Sato et al. Organic Solvent–and Halide–Free Oxidation of Alcohols with Aqueous Hydrogen Peroxide. Journal of the American Chemical Society. 1997, vol. 119 (50) p 12386–12387.*

Sakaguchi et al. Oxidation of Allenes and Alkynes with Hydrogen Peroxide Catalyzed by Cetylpyridinium Peroxotungstophosphate (PCWP). Journal of Organic Chemistry. 1994, vol. 59(19), p 5681–5686.*

* cited by examiner

Primary Examiner—Johann Richter
Assistant Examiner—Sikarl A. Witherspoon
(74) Attorney, Agent, or Firm—Venable LLP; Ann S. Hobbs

(57) ABSTRACT

The present invention relates to an oxidation reaction catalyzed by a reaction controlled phase-transfer catalyst having the general formula of $[R_1R_2R_3R_4N]_xH_y[A]$ or $Q_mMO_3(L)$. The catalysts themselves are not soluble in the reaction medium, but can form an active species that is soluble in the reaction medium under the action of one of the reactants. The active species can in turn react selectively with another reactant. When one of the reactants is completely consumed, the catalyst will separated out from the reacting system and can be recovered by means of simple separation method. The recovered catalyst can be recycled with comparable efficiency as that of the original catalyst. The separation of said catalyst is similar to that of heterogeneous catalyst while said catalyst will completely exhibit the characteristics of homogeneous catalyst during the reaction. The catalytic oxidation reaction system is especially suitable for the large-scale industrial production of epoxy cyclohexane from cyclohexene or of epoxy propane from propylene.

15 Claims, No Drawings

OXIDATION REACTION PROCESS CATALYZED BY PHASE-TRANSFER CATALYST CONTROLLING REACTION

TECHNICAL FIELD

The present invention relates to an oxidation reaction process catalyzed by reaction controlled phase-transfer catalyst, in particular, provides a reaction controlled phase-transfer catalyst used in homogeneous oxidation reaction and an oxidation reaction process.

BACKGROUND ART

Catalytic process is the nuclei of modern chemistry and chemical industrial application. Based on the morphology of the catalyst in the reaction process, catalytic process can be classed as heterogeneous catalytic reaction and homogeneous catalytic reaction. At the present time, most of the chemical industrial processes employ heterogeneous catalytic reaction. However, since homogeneous catalytic reaction has the advantages of higher catalytic activity of catalyst used and milder reaction conditions, it continuously serves as an important branch in fundamental research and industrial applications.

The largest difficulty in the wide application of homogeneous catalytic reaction is that it is difficult to separate and recover the catalyst after the completion of the reaction since the homogeneous catalyst used is completely soluble in the reacting system [*Advances in Homogeneous Catalysis*, Chemical Industry Publisher, Beijing, 1990]. Most of the homogeneous catalysts comprise transition metal that is quite expensive and therefore the problem of separation and recovery of the catalyst will be the key factor determining the economic suitability of the reaction process.

For the moment, there is not yet systematic method for separating and recovering catalyst from reacting system for different kinds of homogeneous catalytic reactions. Some useful attempts have been made in this direction, such as loading the homogeneous catalyst on solid carrier [*Catalysis by Supported Complexes*, 1981], in which homogeneous catalyst is loaded on inorganic carriers (such as $SiO_2$, diatomaceous earth, active carbon etc.) or bonded chemically to organic polymeric carriers (such as chlorine bead of polystyrene series) to form solid catalyst insoluble in reacting system. By doing so, the catalyst can conveniently be separated and recovered after the reaction ended. However, in this method, the catalytic activity of the homogeneous catalyst is significantly lowered. At the same time, the metal loaded on the carrier will easily be fallen off, resulting in the loss of metal. Therefore there had been only a few practical applications.

DISCLOSURE OF THE INVENTION

The objective of the present invention is to overcome the problem generally encountered in separation and recovery of homogeneous catalyst and to provide a novel reaction controlled phase-transfer catalyst together with oxidation reaction process carried out using said catalyst. The catalyst exhibits completely the characteristics of homogeneous catalyst in the reaction process, possesses high catalytic activity, while it can be separated just like heterogeneous catalyst after the completion of the whole process. The recovered catalyst can be recycled and the performance of the recovered catalyst is comparable to that of the original catalyst.

The reaction controlled phase-transfer catalyst provided by the present invention and used in oxidation reaction along with the oxidation reaction process are characterized in that the catalyst used in the reacting system itself is not soluble in the reaction medium, but under the action of one of the fed reactants, it forms an active species that can dissolve in the reaction medium, and the active species formed react selectively with another reactant to yield target product; when said one of the reactants is completely consumed, the catalyst will separate out from the reacting system and can be recovered by means of simple separation method, and the recovered catalyst can be recycled. Taking oxidation reaction as an example, the overall reaction process can be represented by the following equation:

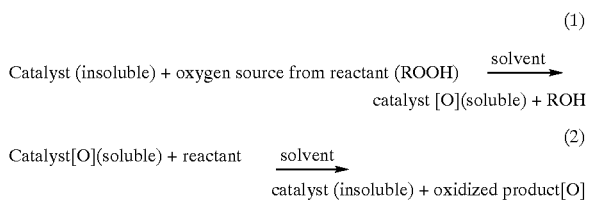

where R=H or alkyl group.

Specifically, the oxidation reaction process catalyzed by the reaction controlled phase-transfer catalyst of the present invention is characterized in that said reaction process comprises the following steps:

(a) employing a reaction controlled phase-transfer catalyst, wherein the catalyst itself is not soluble in the reaction medium, but under the action of one of the reactants, it can form an active species that can dissolve in the reaction medium, and the active species react selectively with another reactant to yield target product; when said one of the reactants is completely consumed, the catalyst will separate out from the reacting system;

(b) reacting oxygen source with substrate to yield product in reaction medium of homogeneous phase or water/oil two phase, under the catalytic action of the reaction controlled phase-transfer catalyst;

(c) separating out reaction controlled phase-transfer catalyst by centrifugation or filtration after the completion of the reaction, wherein the catalyst can be recycled; and (d) carrying out the oxidation reaction at a temperature of −20° C. to 110° C.

In the oxidation reaction, said reaction controlled phase-transfer catalyst is characterized in that said catalyst is heteropolyacid compounds with formula of $[R_1R_2R_3R_4N]_x H_y[A]$, wherein $R_1$, $R_2$, $R_3$, and $R_4$ are linear or branched alkyl, cycloalkyl, or benzyl with $C_1$–$C_{20}$, or $R_1R_2R_3N$ is pyridine or its homologues; A is a heteropolyanion group of P or As containing metal atom of Mo, W or V; x is an integer of from 1 to 9, and y is an integer of from 0 to 8.

Alternatively, said phase-transfer catalyst can also be a complex represented by the general formula of $Q_m MO_3(L)$ (II), wherein M is the central metal atom such as Mo, W etc.; Q is the cation moiety, such as $[R_1R_2R_3R_4N^+]$, in which $R_1$, $R_2$, $R_3$, and $R_4$ are linear or branched alkyl, cycloalkyl, or benzyl with $C_1$–$C_{20}$, or $R_1R_2R_3N$ is pyridine or its homologues; and L is a bidentate ligand containing N or O. When L is N,N-bidentate ligand, it includes $R_1,R_2$-2,2'-dipyridine ($R_1$ and $R_2$ can be substituents such as H—, $C_1$–$C_{20}$ linear or branched alkyl group, cycloalkyl group, aromatic group etc. at the position of 2 to 9), $R_1$, $R_2$, $R_3$-o-phenanthroline ($R_1$, $R_2$, and $R_3$ can be substituents such as H—, $C_1$–$C_{20}$ linear or branched alkyl group, cycloalkyl group, aromatic group etc. at the position of 2 to 9), m=0. When L is N,O-bidentate ligand, it includes 8-hydroxy quinoline, 2-carboxy pyridine, Schiff base formed from salicylaldehyde with primary amine and the like, m=1. When L is O,O-bidentate ligand, it includes β-carbonyl ketone or ester, m=1. Such catalysts themselves are not soluble in the reaction medium, but under the action of oxygen source, they can form oxidated active species that can dissolve in the reaction medium. The oxidated active species reacts with another reactant and selectively oxidizes it to target product. When the oxygen source is completely consumed, the catalyst will separate out from the reacting system and can be conveniently recovered by simple separation method such as centrifugation or filtration. The recovered catalyst can be recycled with comparable performance as that of the original one.

Further, in the reaction controlled oxidation reaction process, the reaction medium used in said reaction includes alcohols such as methanol, ethanol, n-propyl alcohol, isopropyl alcohol, tertiary butyl alcohol and secondary alcohol with branch or dihydroterpineol; paraffinic solvents such as $C_5$–$C_{18}$ straight chain alkane, branched chain alkane, or cycloalkane; aromatic solvents such as benzene, toluene, ethyl benzene, xylene, trimethyl benzene or other monosubstituted or polysubstituted alkyl benzene; ester solvents such as esters of aliphatic acids, esters of aromatic acids, or trimethyl phosphate, triethyl phosphate, tripropyl phosphate, tributyl phosphate, trioctyl phosphate and other trialkyl phosphate; ether solvents such as alkyl ethers, aryl ethers or aryl alkyl ethers; ketone solvents such as dialkyl ketones, aryl alkyl ketones; nitrile solvents such as acetonitrile, benzyl nitrile; and halogenated hydrocarbon solvents such as halogenated alkanes and halogenated aromatic hydrocarbons. These solvents can be used alone or in a combination.

In the oxidation reaction, the oxygen source used is hydrogen peroxide ($H_2O_2$) or alkyl hydroperoxide (ROOH).

In the oxidation reaction, the hydrogen peroxide used is 5% to 90% aqueous solution of hydrogen peroxide; and the alkyl hydroperoxide used is tertiary butyl hydroperoxide, ethylphenyl hydroperoxide, cumenyl hydroperoxide or cyclohexyl hydroperoxide. The aqueous solution of hydrogen peroxide or solution of alkyl hydroperoxide can be directly added as oxygen source.

In the oxidation reaction, when the hydrogen peroxide used is formed in-situ from the oxidation reaction of substituted hydroquinone, after the completion of the reaction and separation of the catalyst, product and unreacted raw materials, the substituted hydroquinone could be regenerated by reacting substituted quinone with hydrogen under the action of hydrogenation catalyst of transition metal.

The substituted hydroquinone used in the reaction process has the following general structure:

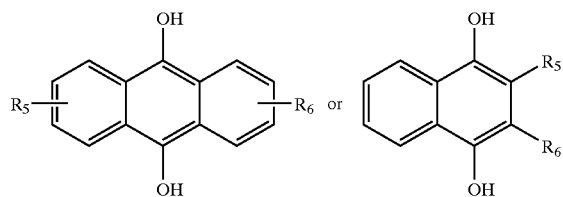

wherein $R_5$ and $R_6$ are H or $C_1$–$C_{10}$ alkyl group. It is also possible to use a mixture of two or more said substituted hydroquinones to generate hydrogen peroxide in-situ.

The hydrogenation catalysts of transition metal are those containing palladium, platinum, chromium, rhodium, nickel or ruthenium. These catalysts can be prepared by conventional methods.

In the oxidation reaction, the substrate concerned is alkene, alkane, aromatic hydrocarbon, ketone, alcohol, thioether or sulfoxide, and the oxidation reaction taken place is epoxidation of alkene, cleavage oxidation of alkene into aldehyde, ketone or carboxylic acid, hydroxylation of alkane, hydroxylation of aromatic hydrocarbon, oxidation of alcohol into ketone, oxidation of ketone into ester, oxidation of thioether into sulfoxide or oxidation of sulfoxide into sulfone.

The alkene substrates useful in said epoxidation of alkene include those organic compounds having at least one C=C double bond such as aromatic alkenes, aliphatic alkenes, aryl alkyl alkenes, cyclo-alkenes, inear or branched alkenes, such as propylene, 1-butene, 2-butene, isobutylene, cyclopentene, cyclohexene, styrene etc.; or dienes, trienes and unsaturated compounds containing more C=C double bonds, or unsaturated polymers; or derivatives of unsaturated aliphatic acids and their esters or glycerides. Besides alkyl substituents, the alkene substrates can also contain other substituents, such as halogen, carboxy, ester group, alkoxy, hydroxyl, mercapto, nitro, nitrile group, acyl or amino, with the examples of chloropropylene, allyl alcohol, phenyl allyl ether. The substrates of the epoxidizing reaction can be used alone or in a combination.

The substrates useful in said cleavage oxidation reaction of alkene into aldehyde, ketone or carboxylic acid could be in the same range as that for the epoxidation of alkene.

The substrates useful in said hydroxylation of alkane include linear alkanes, branched alkanes, cycloalkanes and substituted cycloalkanes of $C_5$–$C_{30}$. The substituents can include halogen, carboxy, ester group, alkoxy, hydroxyl, mercapto, nitro, nitrile group, acyl or amino.

The substrates useful in said hydroxylation of arene include arenes and substituted arenes of $C_6$–$C_{30}$. Besides the hydrocarbon substituents, the substituents also include halogen, carboxy, ester group, alkoxy, hydroxyl, mercapto, nitro, nitrile group, acyl or amino.

The reaction substrates useful in said oxidation of alcohol into aldehyde or ketone include aromatic alcohols, aliphatic alcohols, aryl alkyl alcohols, cycloalkyl alcohols, linear alcohols or branched alcohols. In addition, glycols could also be oxidized into corresponding aldehydes or ketones.

The substrates useful in said oxidation reaction of ketone to ester include aromatic ketones, aliphatic ketones, aryl alkyl ketones, cyclic ketones, straight chain ketones or branched chain ketones.

The substrates useful in said oxidation reaction of thioether to sulfoxide include aromatic thioethers, aliphatic thioethers, aryl alkyl thioethers, cyclic thioethers, straight chain thioethers or branched chain thioethers.

The substrates useful in said oxidation reaction of sulfoxide to sulfone include aromatic sulfoxides, aliphatic sulfoxides, aryl alkyl sulfoxides, cyclic sulfoxides, straight chain sulfoxides or branched chain sulfoxides.

In the different kinds of oxidation reaction of the present invention, the reaction conditions are mild and the reaction temperature is in the range of from −20° C. to 110° C., preferably in the range of from 30° C. to 100° C. In addition, the ratio of substrate to hydrogen peroxide or alkyl hydrogen peroxide can be in the range of from 1:100 to 100:1, preferably in the range of from 1:10 to 10:1.

The oxidation reaction process of the present invention is suitable for the industrial production of epoxy cyclohexane from cyclohexene through catalytic epoxidation. The catalyst used is the reaction controlled phase-transfer catalyst that is the above-defined heteropolyacid compounds. Oxygen source is aqueous solution of hydrogen peroxide or in-situ formed hydrogen peroxide. In organic solvent and in the presence of the catalyst, cyclohexene is selectively converted into epoxy cyclohexane through catalytic epoxidation. The temperature of the epoxidation is in the range of from 30° C. to 100° C.

Furthermore, the present oxidation reaction process is also suitable for preparing epoxy propane from propylene through catalytic epoxidation.

In addition, the oxygen source used in the epoxidizing reaction process can be consumed completely during the epoxidation. If residual oxygen source is left after the completion of the epoxidizing reaction, it may be completely consumed through elevating the system temperature or adding reductive solution in order that catalyst (I) could be separated and recovered completely to be recycled.

In the case where residual oxygen source is left after the completion of the epoxidizing reaction and the treatment of elevating the system temperature is employed to consume the excess oxygen source, the temperature is in a range of 60° C. to 100° C., preferably in a range of 70° C. to 90° C.

In the case where residual oxygen source is left after the completion of the epoxidizing reaction, it is also possible to add reductive aqueous solution to the reacting system to treat the excess oxygen source. The reductive solutions can be dilute aqueous solution of $Na_2SO_3$, $Na_2S_2O_3$, $NaHSO_3$ etc.

The present epoxidizing reaction process is simple and easy to be carried out and can prepare epoxy cyclohexane or epoxy propylene at high efficiency and high selectivity. The used catalyst could conveniently be separated out, recovered and recycled. In the whole process, only cyclohexene or propylene, hydrogen peroxide or air and hydrogen are consumed. The cost of the process is low and the final product is exclusively epoxy cyclohexane or epoxy propane without by-product. The process is simple in the post-treatment and relatively friendly to the environment, can meet the technical and economical requirements and solve the above-mentioned problem of difficulties in separation and recovery of the homogeneous catalyst. Therefore, the process indeed is a novel approach suitable to produce epoxy cyclohexane or epoxy propane in large-scale industry.

As mentioned above, the novel reaction controlled phase-transfer catalyst provided by the present invention can selectively convert a wide range of substrates into corresponding oxidized product through catalytic oxidation. During the reaction process, said catalyst is soluble in the reacting system and exhibits completely the characteristics and action of a homogeneous catalyst. Thus the reaction conditions are mild. After the completion of the whole reaction, the catalyst will separate out from the reacting system due to lack of oxygen source. Therefore, separation of the catalyst is similar to that of the heterogeneous catalyst and the problem of difficulties in separation and recovery of the homogeneous catalyst is solved. The present process could meet the technical and economical requirements and provide a novel catalyst system and a reaction process suitable for large-scale industrial applications.

Specific Embodiments

The following examples are given to illustrate the present invention in more detail. Naturally, the present invention is not limited by these concrete examples.

EXAMPLE 1

Epoxidation of Cyclohexene 40 mmol of cyclohexene was dissolved in 40 mL mixed trimethylbenzene and then 20 mmol of 15% (w/w) aqueous solution of $H_2O_2$ and 0.2 mmol of catalyst $[(C_2H_5)_2NCH_2Ph]_2HAsMo_2O_{10}$ were added. The reaction was carried out at 65° C. for 1 hour. The conversion of the cyclohexene was 49.0% and the selectivity of the epoxy cyclohexane was 95.2%. At that time, the catalyst separated out from the reacting system and was recovered by centrifugation and vacuum dried. The unreacted raw material cyclohexene and the product epoxy cyclohexane were distilled out from the organic layer. To the residue of the distillation, recovered epoxidizing catalyst, cyclohexene and hydrogen peroxide were again added and the above reaction was carried out cyclically. The results of the reaction were shown in the following table.

The recovered catalyst was used 5 times cyclically and the results were shown in the following table.

| Cycle No. of the catalyst | Conversion of cyclohexene % | Selectivity of epoxy cyclohexane % |
|---|---|---|
| fresh catalyst | 49.0 | 95.2 |
| I | 48.6 | 96.0 |
| II | 48.2 | 96.5 |
| III | 48.7 | 95.7 |
| IV | 48.5 | 95.8 |
| V | 48.6 | 95.7 |

When the solvent, oxygen source, catalyst of the reacting system were varied and the other conditions were identical with those of Example 1, the results obtained from the epoxidizing reaction were shown in the following table.

| Solvent | $O_2$ source | Catalyst | T ° C. | Conversion of cyclohexene % | Selectivity of epoxy cyclohexane % |
|---|---|---|---|---|---|
| Tertiary butanol | 35% $H_2O_2$ solution | $[(C_6H_{12})(C_2H_5)_2NH]_3[PMo_4O_{16}]$ | 50 | 45.6 | 93.7 |
| Cyclohexane | t-Butyl hydroperoxide solution | $[(2-C_3H_7)_4N]_2HAsW_2O_{10}$ | 45 | 35.8 | 95.2 |
| Triethyl phosphate | Cumenyl hydroperoxide in cumene | $[(CH_3)_3NCH_2Ph]_2HPMo_2O_{10}$ | 55 | 46.7 | 93.1 |
| Phenylmethyl ether | 65% $H_2O_2$ solution | $[\delta\text{-}C_5H_5NC_4H_9]_7PV_4O_{16}$ | 30 | 47.9 | 88.7 |
| Acetophenone | Ethylphenyl hydroperoxide solution | $[(2-C_4H_9)\text{-}(\delta\text{-}C_5H_4N)(C_6H_{13})]_3[PMo_4O_{16}]$ | 35 | 38.9 | 82.7 |

| Solvent | O$_2$ source | Catalyst | T °C. | Conversion of cyclohexene % | Selectivity of epoxy cyclohexane % |
|---|---|---|---|---|---|
| Benzyl nitrile | 50% H$_2$O$_2$ solution | [(t-C$_4$H$_9$)$_2$N(C$_2$H$_5$)$_2$]$_3$AsW$_2$O$_{10}$ | 35 | 48.6 | 94.6 |
| Chloroform | Cyclohexanyl hydroperoxide solution | [δ-C$_5$H$_5$NC$_{12}$H$_{25}$]$_2$HPMo$_2$O$_{10}$ | 45 | 49.0 | 96.8 |

When the solvent, olefin and temperature were changed and the other conditions were identical with those of Example 1, the results of the epoxidation were shown in the following table.

| Olefine | Solvent | Temperature °C. | Conversion % | Selectivity % |
|---|---|---|---|---|
| Cyclooctene | Methyl t-butyl ether | 30 | 43 | 94.6 |
| 2-Octene | Phenyl methyl ether + Toluene | 45 | 46.2 | 95 |
| Soya bean oil | Toluene | 60 | 42.1 | 95 |
| Styrene | o-Dichlorobenzene | 45 | 38 | 92 |
| α-Methylstyrene | Chloroform | 40 | 40 | 96.3 |

EXAMPLE 2

Epoxidation of Cyclohexene 20 mmol of 2-methylnaphthoquinone was dissolved in mixed solvent of 15 mL dimethyl phthalate and 15 mL diisobutyl methanol and then 2% of 5% Pd/C (w/w) catalyst was added. The reaction was carried out at 6 atm of hydrogen and 45° C. for 6 hours to hydrogenate 2-methylnaphthoquinone to a degree of 50%. At that time, hydrogenation was stopped and the Pd/C catalyst was removed by filtration. Then to the filtrate were added 30 mmol of cyclohexene and 0.09 mmol of catalyst [δ-C$_5$H$_5$NC$_4$H$_9$]$_7$PV$_4$O$_{16}$. The reaction was performed at 1 atm of O$_2$ and 65° C. for 2 hours. At that time, the catalyst had already separated out from the reacting system. The conversion of cyclohexene was 33.0% and the selectivity of the epoxy cyclohexane was 98.3%. The catalyst was recovered by suction filtration and was dried in air at room temperature. The unreacted raw material cyclohexene and the product epoxy cyclohexane were distilled out. To the residue of the distillation was added 2% of Pd/C (W/W) catalyst, and catalytic hydrogenation was performed as described above. Then the recovered epoxidizing catalyst and cyclohexene were again added to the system and the above reaction was carried out cyclically. The results of the reaction were shown in the following table.

| Cycle No. of the catalyst | Conversion of cyclohexene % | Selectivity of epoxy cyclohexane % |
|---|---|---|
| Fresh catalyst | 33.0 | 98.3 |
| I | 33.1 | 97.5 |
| II | 32.8 | 97.9 |
| III | 32.7 | 97.2 |
| IV | 32.8 | 97.3 |
| V | 32.7 | 97.0 |

When the solvent, reducing agent and hydrogenating catalyst were changed and the other conditions were identical with those of the Example 2, the results of the epoxidizing reaction were shown in the following table.

| Solvent | Reducing agent | Hydrogenating catalyst | Conversion of cyclohexene % | Selectivity of epoxy cyclohexane % |
|---|---|---|---|---|
| β-methyl naphthalene + trioctyl phosphate | Hydrazo-benzene | Raney Ni | 32.8 | 98.2 |
| 1,3,5-Trimethylbenzene + dihydroterpineol | 2-Ethyl anthraquinone | Pd/Al$_2$O$_3$ | 33.3 | 96.4 |
| Phenyl methyl ether + diethyl phthalate | Hydroquinone | Pt/Al$_2$O$_3$ | 29.5 | 98.7 |
| C$_9$ aromatic hydrocarbon + methylcyclohexyl acetate | 2,5-Diethyl hydrogenated pyrazine | Ru/C | 24.3 | 96.8 |

EXAMPLE 3

Epoxidation of Cyclohexene 20 mmol of cyclohexene was dissolved in 40 mL of t-butyl alcohol and to the solution, 40 mmol of 30%(W/W) aqueous hydrogen peroxide and 0.05 mmol of catalyst

[(CH$_3$)$_3$NCH$_2$Ph]$_2$HPMo$_2$O$_{10}$ were added. The reaction was carried out at 50° C. for 3 hours. The conversion of the cyclohexene was 47.6% and the selectivity of the epoxy cyclohexane was 94.7%. Then 10% Na$_2$SO$_3$ aqueous solution was used to decompose the unreacted H$_2$O$_2$. At that time, catalyst separated out from the reacting system and was recovered. Unreacted raw material cyclohexene and product cyclohexane were distilled out from the organic layer. To the tertiary butyl alcohol obtained from the distillation, the recovered epoxidizing catalyst, cyclohexene and hydrogen peroxide were again added to carry out the above reaction cyclically.

EXAMPLE 4

Epoxidation of Cyclohexene 40 mmol of 2-ethylanthraquinone was dissolved in a mixture of 19 mL of 1,3,5-trimethyl benzene and 17 mL dihydroterpineol. To the solution was added 10% Cu/SiO2 (W/W) catalyst. The reaction was carried out at 6 atm of H$_2$ and 45° C. for 6 hours to hydrogenate 2-ethylanthraquinone to a degree of 50%. Then hydrogenation was stopped and the Pd/C catalyst was removed by filtration. To the filtrate, 30 mmol of cyclohexene and 0.2 mmol of [(n-C$_6$H$_{13}$)$_4$N]$_7$PV$_4$O$_{16}$ were added successively. The reaction was carried out at 60° C. for 2 hours and the catalyst separated out from the reacting system. The conversion of cyclohexene was 65.3% and the selectivity of the epoxy cyclohexane was 97%. The separated catalyst was recovered by filtration and was vacuum dried. Unreacted raw material cyclohexene and product cyclohexane were distilled out. To the residue of the distillation was added 10% Pd/C (W/W) catalyst and the hydrogenating reaction was carried out at 6 atm of H$_2$ and 55° C. for 4 hours. Pd/C catalyst was then filtered off. To the filtrate, the recovered epoxidizing catalyst and cyclohexene were added to carry out the above reaction cyclically.

EXAMPLE 5

Epoxidation of Propylene 20 mmol of 2-t-butylanthraquinone was dissolved in a mixture of 15 mL of mixed trimethyl benzene and 15 mL tributyl phosphate, then to the solution was added 0.125 g of 5% Pd/C catalyst. The hydrogenating reaction was carried out at 6 atm of H$_2$ and 45° C. until 10 mmol of 2-t-butylanthrahydroquinone was formed, then the Pd/C catalyst was filtered off. O$_2$ was passed into the mother liquor to complete oxidation to form hydrogen peroxide and 2-t-butylanthraquinone. The oxidized liquor was transferred into a glass-lined autoclave. 0.09 mmol of [δ-C$_5$H$_5$NC$_{12}$H$_{25}$]$_3$[PW$_4$O$_{16}$] was added and 60 mmol of propylene was charged into the autoclave. The reaction was carried out at 50° C. for 4 hours. The conversion of propylene relative to 2-t-butylanthrahydroquinone was 90% and the selectivity of epoxy propane was 95%. The separated catalyst after reaction was recovered by centrifugation and was used in the next reaction. Unreacted propylene, epoxy propane and water were separated from the reacting mother liquor, and 2-t-butylanthraquinone could be catalytically hydrogenated in the presence of 5% Pd/C catalyst to yield 2-t-butylanthrahydroquinone again. The results obtained by recycling catalyst for 3 times were shown in the following table.

| Cycle No. of the catalyst | Conversion of propylene (relative to hydroquinone) % | Selectivity of epoxy propane (relative to propylene) % |
|---|---|---|
| Fresh catalyst | 90 | 95 |
| I | 89 | 93 |
| II | 89 | 94 |
| III | 88 | 91 |

Other reaction controlled phase-transfer catalysts could also be used to catalyze the epoxidation of propylene. The results obtained in epoxidizing reaction with other experimental conditions being same as those used in Example 5 were shown in the following table.

| Solvent | Catalyst | Reducing agent | T ° C. | Conversion of ropylene (relative to reducing agent), % | Selectivity of epoxy propane (relative to propylene), % |
|---|---|---|---|---|---|
| Toluene + trioctyl phosphate | [(C$_6$H$_{12}$)$_4$N]$_3$ [PMo$_4$O$_{16}$] | 2-Ethylanthrahydroquinone | 75 | 40 | 96 |
| Dimethyl phthalate + Triethyl Phosphate | [δ-C$_5$H$_5$NC$_{16}$H$_{33}$]$_3$ [PW$_3$O$_{13}$] | 2-Butylanthrahydroquinone | 55 | 90 | 95 |
| t-Butyl alcohol | [(C$_2$H$_5$)$_3$NCH$_2$Ph]$_3$ [AsW$_{12}$O$_{40}$] | hydrazo-benzene | 55 | 83 | 91 |
| C$_9$ Arene + Methyl cyclohexyl acetate | [(C$_4$H$_9$)$_3$NCH$_2$Ph]$_7$ [PW$_{11}$O$_{39}$] | 2,5-Diethyl hydrogenated pyrazine | 60 | 88 | 88 |
| Xylene + Dihydroterpineol | [δ-C$_5$H$_5$NC$_{14}$H$_{29}$]$_9$ [AsW$_9$O$_{34}$] | 2,3-Diethyl naphthohydroquinone | 35 | 90 | 82 |

EXAMPLE 6

Epoxidation of Olefins

Example 5 was repeated except that solvent, olefin, temperature and reducing agent used to yield H$_2$O$_2$ of the reacting system were changed, and the results of the epoxidizing reaction were shown in the following table.

| Olefin | Reducing agent | Solvent | T °C. | Conversion % | Selectivity % |
| --- | --- | --- | --- | --- | --- |
| Chloropropylene | 2-ethylanthrahydroquinone | Tripropyl phosphate + Ethylbenzene | 65 | 83 | 81 |
| 1-Dodecene | 3-ethyl-2-methyl-naphthohydroquinone | Dimethyl phthalate + Toluene + Di-iso-butyl methanol | 60 | 85 | 87 |
| α-Naphthylallyl ether | 2-butylanthra-hydroquinone | 1,2-Dichloroethane + Tributyl phosphate | 50 | 92 | 90 |

Upon the completion of reaction, the catalysts all separated out from the system in form of precipitate that could be recovered by simple filtration or centrifugation and recycled. The reducing agent used in the reaction was oxidized during the reaction, and could be regenerated by catalytic hydrogenation after reaction and recycled.

EXAMPLE 7

Oxidation of 2-Butanol for the Preparation of 2-Butanone 40 mmol of 2-butanol was dissolved in 50 mL dichloroethane. To the solution were added 20 mmol of 35%(W/W) aqueous hydrogen peroxide and 0.2 mmol of catalyst $[(C_2H_5)_3NCH_2Ph]_2HAsMo_2O_{10}$. The reaction was carried out at 65° C. for 1 hour. The conversion of 2-butanol was 31.0% and the selectivity of 2-butanone was 88.2%. At this time, the catalyst separated out from the reacting system and was recovered by centrifugation and then vacuum dried. The recovered catalyst was recycled 3 times in the above reaction and the results were shown in the following table.

| Cycle No. of the catalyst | Conversion of 2-butanol % | Selectivity of 2-butanone % |
| --- | --- | --- |
| Fresh catalyst | 31.0 | 88.2 |
| I | 30.6 | 89.0 |
| II | 31.2 | 88.0 |
| III | 31.7 | 88.1 |

Example 7 was repeated except that the substrate, solvent and temperature of the reaction system were changed, and the results of the oxidation reaction were shown in the following table.

| Alcohol | Product | Solvent | T °C. | Conversion, % | Selectivity, % |
| --- | --- | --- | --- | --- | --- |
| α-Phenethyl alcohol | Acetophenone | cyclohexane | 55 | 32.0 | 92.3 |
| β-Phenethyl alcohol | Phenylacet-aldehyde | Acetonitrile | 80 | 20.3 | 67.9 |
| Cyclohexanol | Cyclohexanone | t-Butanol | 80 | 30.1 | 89.3 |
| 1-Octanol | Octanone | t-Butanol | 90 | 26.4 | 93.3 |
| Isobutanol | Isobutanone | Ethylbenzene | 50 | 30.3 | 95.6 |
| 3-Hexanol | 3-Hexanone | 1,2,3-Trichloropropane | 55 | 25.3 | 92 |

EXAMPLE 8

Epoxidation of 1-Heptene 20 mmol of 2-ethylanthraquinone was dissolved in a mixture of 15 mL of $C_9$ arene and 15 mL of methylcyclohexyl acetate. To the solution was added 2% of 5% Pd/C (W/W) catalyst. The reaction was carried out at 6 atm of hydrogen and 45° C. for 6 hours to hydrogenate 2-ethylanthraquinone to a degree of 50%, then the hydrogenation was stopped and the Pd/C catalyst was removed by filtration. To the filtrate were added 30 mmol of 1-heptene and 0.09 mmol of catalyst $[(n-C_8H_{17})_4N]_2HAsW_2O_{10}$. The reaction was carried out at 1 atm of $O_2$ and 65° C. for 6 hours. At this time, the catalyst had separated out from the reacting system and the conversion of 1-heptene was 31.0% and the selectivity of 1,2-epoxy heptane was 93.7%. The catalyst was recovered by suction filtration, dried in air at room temperature and used cyclically in the above reaction for 3 times. The results of the reaction were shown in the following table.

| Cycle No. of the catalyst | Conversion of 1-heptene % | Selectivity of 1,2-epoxy heptane % |
| --- | --- | --- |
| Fresh catalyst | 31.0 | 93.7 |
| I | 31.1 | 92.5 |
| II | 30.8 | 93.9 |
| III | 30.7 | 93.2 |

EXAMPLE 9

Oxidation of Isoeugenol (1) and trans-Ferulic Acid (2) for Preparing Vanillin (3)

30.5 mmol of 1 or 2 was dissolved in 40 mL of t-butyl alcohol. To the solution was added 91.5 mmol of 85% $H_2O_2$ aqueous solution (W/W). The reacting solution was dried over anhydrous $MgSO_4$. Then 0.3 mmol (1 mol %) of $[(t-C_4H_9)_4N]_3PMo_4O_{16}$ catalyst was added. The reaction was carried out at 60° C. for 2 hours. Both of the conversion of 1 and 2 were 100% and the yield of 3 was larger than 60%. After the unreacted $H_2O_2$ was decomposed by adding 10% $NaHSO_3$ aqueous solution, the catalyst separated out from the reacting system and was recovered by centrifugation. The recovered catalyst was vacuum dried at a temperature below 50° C. and could be recycled in the above reaction.

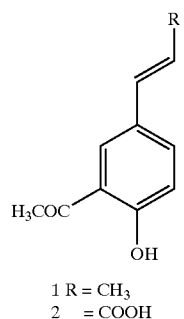

1 R = $CH_3$
2    = COOH mol/L solution of cumenyl hydroperoxide in cumene and then 0.1 mmol of catalyst (I). The reaction was conducted at 0° C. for 2 hours. At this time, catalyst separated out from the reacting system. The conversion of methyl phenyl thioether was 24.3% and the yield of methyl phenyl sulfoxide was 23.1%. After the separated catalyst was recovered by filtration and vacuum dried, it could be recycled in the above reaction.

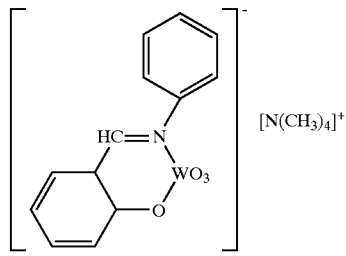

(I)

Example 10 was repeated except that the substrate, solvent, catalyst and reaction temperature of the reacting system were changed, and the results of the reaction were shown in the following table.

| Thioether | Solvent | Catalyst | T °C. | Conversion, % | Selectivity, % |
|---|---|---|---|---|---|
| Methyl phenyl thioether | Ethyl benzoate | $[C_{12}H_{25}N(C_2H_5)_3]_3[AsW_4O_{16}]$ | 0 | 24.8 | 93 |
| Dipropyl thioether | Isoamyl benzoate | $[C_6H_{13}N(C_2H_5)_3]_9[AsW_9O_{34}]$ | 20 | 21.5 | 88 |
| Methyl t-butyl thioether | n-Octane | $[(C_4H_9)_3NCH_2Ph]_3[PW_{12}O_{40}]$ | 15 | 23.3 | 86 |
| Tetrahydro-thiopene | Toluene | $[\delta\text{-}C_5H_5NC_6H_{12}]_5H_2[AsW_{11}O_{39}]$ | 30 | 24 | 92 |

-continued

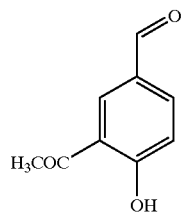

3

EXAMPLE 10

Oxidation of Methyl Phenyl Thioether for Preparing Methyl Phenyl Sulfoxide 40 mmol of methyl phenyl thioether was dissolved in 20 mL of chloroform. To the solution was added 10 mmol of 1

EXAMPLE 11

Oxidation of Sulfoxide for Preparing Sulfone 40 mmol of methyl phenyl sulfoxide was dissolved in 20mL of n-pentane. To the solution was added 20 mmol of 85% aqueous solution of hydrogen peroxide and then 0.1 mmol of catalyst $[(n-C_4H_9)_4N]_3[AsW_{12}O_{40}]$. The reaction was conducted at 0° C. for 2 hours. At this time, catalyst separated out from the reacting system. The conversion of methyl phenyl sulfoxide was 44.7% and the yield of methyl phenyl sulfone was 40.1%. After the separated catalyst was recovered by filtration and vacuum dried, it could be recycled in the above reaction.

Example 11 was repeated except that the substrate, solvent and reaction temperature of the reacting system were changed, and the results of the oxidation reaction were shown in the following table.

| Sulfoxide | Solvent | Temperature °C. | Conversion % | Selectivity % |
| --- | --- | --- | --- | --- |
| Dimethyl sulfoxide | Cyclohexane | 5 | 43.2 | 88 |
| Methyl iso-butyl sulfoxide | t-Butanol | 15 | 42.3 | 94 |
| Tetramethylene sulfoxide | 1,2-Dichloroethane | 0 | 43.5 | 96 |

EXAMPLE 12

Oxidation of 1-Methylcyclohexene for Preparing n-Enanthic acid-6-one 10 mmol of 1-methylcyclohexene was dissolved in 20 mL of t-butanol. To the solution was added 40 mmol of 15% (W/W) aqueous solution of hydrogen peroxide and then 0.05 mmol of catalyst $[(n-C_6H_{13})_4N]_2HPMo_2O_{10}$. The reaction was conducted at 80° C. for 24 hours. The yield of n-enanthic acid-6-one was 90%. Then 10% aqueous solution of $NaHSO_3$ was used to decompose the unreacted $H_2O_2$. At this time, the catalyst separated out from the reacting system and was recovered by centrifugation and vacuum dried. It could be recycled in the above reaction.

Example 12 was repeated except that the substrate of the reacting system was changed and the results of the oxidation reaction were shown in the following table.

| Olefin | Product | Conversion % | Selectivity % |
| --- | --- | --- | --- |
| Cyclohexene | Adipic acid | 65.4 | 68.9 |
| 1,2-Dimethyl-1,2-diphenyl-ethylene | Acetophenone | 75.6 | 82.0 |

Example 13

Oxidation of Cyclohexanone for Preparing Caprolactone 40 mmol of cyclohexanone was dissolved in 40 mL acetonitrile. To the solution was added 10 mmol of 50% aqueous solution of $H_2O_2$ (W/W) and then 0.2 mmol of catalyst $[(CH_3)_3NCH_2Ph]_7PV_4O_{16}$. After reacting at 25° C. for 28 hours, the catalyst separated out from the reacting system. The conversion of cyclohexanone was 18% and the selectivity of the caprolactone was 92%. The separated catalyst was recovered by filtration, vacuum dried and could be recycled to the above reaction.

Example 13 was repeated except that the substrate of the reacting system was changed and the results of the oxidation reaction were shown in the following table.

| Ketone | Product | Oxidizing agent | T °C. | Conversion % | Selectivity % |
| --- | --- | --- | --- | --- | --- |
| Acetone | Methyl acetate | Cyclohexanyl hydroperoxide | 60 | 15 | 84 |
| 2-Octanone | Hexyl acetate | 65% Aqueous solution of $H_2O_2$ | 45 | 13 | 90 |
| 4-Methyl-2-heptanone | Isobutyl acetate | α-Ethylphenyl hydroperoxide | 45 | 16.5 | 88 |

EXAMPLE 14

Oxidation of Cyclohexane for Preparing Cyclohexanol and Cyclohxanon

To 43 mL of cyclohexane were added 40 mmol of 35% aqueous solution of $H_2O_2$ (W/W) and 1 mmol of $[N(C_6H_{13})_4]_5[PV_2O_{10}]$. After reacting at 65° C. for 12 hours, the catalyst separated out from the reacting system. The conversion of cyclohexane was 55% (relative to hydrogen peroxide). The selectivity of the cyclohexanol was 31% and that of cyclohexanone was 57%. The separated catalyst was recovered by filtration, vacuum dried and could be recycled in the above reaction.

INDUSTRIAL APPLICABILITY

The above examples illustrate that in appropriate reaction medium and under conditions specified by the present invention, catalytic oxidation reaction can be performed at high efficiency and high selectivity using the novel reaction controlled phase-transfer catalysts according to the present invention. The oxygen source used can be either hydrogen peroxide ($H_2O_2$) directly added, or hydrogen peroxide produced in-situ through oxidation reaction in which an oxygen acceptor having reversible redox properties is used as reducing agent and $H_2O_2$ can be produced in-situ under the action of air. The reducing agent can be regenerated from its oxidized product through simple catalytic hydrogenation and recycled. During the oxidation reaction, the catalyst is soluble in the reacting system and exhibits completely the characteristics and action of homogeneous catalyst, therefore the reaction conditions are mild. After the completion of the whole reaction, oxygen source is completely consumed and the catalyst turns to be insoluble in the reacting system, therefore it could be easily separated, recovered and recycled. In addition, the oxidation process of the present invention is especially suitable for the preparation of epoxy cyclohexane by catalytic epoxidizing reaction of cyclohexene or for the preparation of epoxy propane by oxidation reaction of propylene. In the course of the whole reaction, what are consumed are only cyclohexene or propylene, and $H_2O_2$ or air and $H_2$, therefore the cost of production is low. The final product is exclusively epoxy cyclohexane without by-product and thus the process is friendly to the environment. The reaction process is simple and easily workable, can meet the technical and economical requirements and is indeed a novel approach for the large-scale production of epoxy cyclohexane or epoxy propane.

What is claimed is:

1. An oxidation reaction process catalyzed by reaction controlled phase-transfer catalyst, characterized in that the reaction process comprises the steps of:
   (a) reacting an oxygen source with a substrate in the presence of a reaction controlled phase-transfer catalyst at a temperature of −20° C. to 110° C. in reaction medium of a homogeneous phase or water/oil two phase, to yield a product; and
   (b) separating out the reaction controlled phase-transfer catalyst by centrifugation or filtration after the completion of the reaction, wherein the catalyst can be recycled;

wherein the reaction controlled phase-transfer catalyst is
heteropolyacid compounds with formula of $[R_1R_2R_3R_4N]_xH_y[A]$, wherein $R_1$, $R_2$, $R_3$, and $R_4$ are independently $C_1$–$C_{20}$ linear or branched alkyl, cycloalkyl, or benzyl; or $R_1R_2R_3N$ is pyridine or its homologue; A is a heteropolyanion group of P or As containing metal atom of Mo, W or V; x is an integer of from 1 to 9, and y is an integer of from 0 to 8, with the proviso that said heteropolyacid compounds do not contain active oxygen prior to their use in the oxidation reaction; or
a complex represented by the general formula of $Q_mMO_3(L)$, wherein M is a central metal atom selected from the group consisting of Mo and W atom; Q is a cation moiety of formula $[R_1R_2R_3R_4N^+]$, in which $R_1$, $R_2$, $R_3$, and $R_4$ are $C_1$–$C_{20}$ linear or branched alkyl, branched alkyl, cycloalkyl, or benzyl, or $R_1R_2R_3N$ is pyridine or its homologue; and L is a bidentate ligand containing N or O; when L is N,N-bidentate ligand, it includes $R_1,R_2$-2,2'-dipyridine ($R_1$ and $R_2$ can be substituents such as H—, $C_1$–$C_{20}$ linear or branched alkyl group, cycloalkyl group, aryl group etc. at the position of 2 to 9), $R_1$, $R_2$, $R_3$-o-phenanthroline ($R_1$, $R_2$, and $R_3$ can be substituents such as H—, $C_1$–$C_{20}$ linear or branched alkyl group, cycloalkyl group, aryl group etc. at the position of 2 to 9), m=0; when L is N,O-bidentate ligand, it includes 8-hydroxy quinoline, 2-carboxy pyridine, Schiff base formed from salicylaldehyde or substituted salicylaldehyde with primary amine and the like, m=1; when L is O,O-bidentate ligand, it includes β-carbonyl ketone or ester, m=1.

2. The oxidation reaction process according to claim 1, characterized in that the oxidation reaction is epoxidation of alkene, cleavage oxidation of alkene to aldehyde, ketone or carboxylic acid, hydroxylation of alkane, hydroxylation of aromatic hydrocarbon, oxidation of alcohol to ketone, oxidation of ketone to ester, oxidation of thioether to sulfoxide or oxidation of sulfoxide to sulfone.

3. The oxidation reaction process according to claim 2, characterized in that:
the alkene substrates useful in said epoxidation of alkene include aromatic alkenes, aliphatic alkenes, aryl alkyl alkenes, cyclic alkenes, linear or branched alkenes having at least one C=C double bond; dienes, trienes, unsaturated compounds containing more C=C double bonds, or unsaturated polymers; or derivatives of unsaturated aliphatic acids and their esters or glycerides, wherein besides alkyl substituents, the alkene substrates can contain other substituents, such as halogen, carboxy, ester group, alkoxy, hydroxyl, mercapto, nitro, nitrile group, acyl or amino, and the substrates of the epoxidizing reaction can be used alone or in a combination;
the substrates useful in said cleavage oxidation reaction of alkene to aldehyde, ketone or carboxylic acid are in the same range as that for the epoxidation of alkene;
the substrates useful in said hydroxylation of alkane include linear alkanes, branched alkanes, cycloalkanes and substituted cycloalkanes of $C_5$–$C_{30}$, wherein the substituents can include halogen, carboxy, ester group, alkoxy, hydroxyl, mercapto, nitro, nitrile group, acyl or amino;
the substrates useful in said hydroxylation of aromatic hydrocarbon include arenes and substituted arenes of $C_6$–$C_{30}$, wherein besides the hydrocarbon substituents, the substituents include halogen, carboxy, ester group, alkoxy, hydroxyl, mercapto, nitro, nitrile group, acyl or amino;
the substrates useful in said oxidation of alcohol to aldehyde or ketone include aromatic alcohols, aliphatic alcohols, aryl alkyl alcohols, cycloalkyl alcohols, linear alcohols or branched alcohols, and glycols can also be oxidized into corresponding aldehydes or ketones;
the substrates useful in said oxidation of ketone to ester include aromatic ketones, aliphatic ketones, aryl alkyl ketones, cyclic ketones, straight chain ketones or branched chain ketones;
the substrates useful in said oxidation of thioether to sulfoxide include aromatic thioethers, aliphatic thioethers, aryl alkyl thioethers, cyclic thioethers, straight chain thioethers or branched chain thioethers;
the substrates useful in said oxidation of sulfoxide to sulfone include aromatic sulfoxides, aliphatic sulfoxides, aryl alkyl sulfoxides, cyclic sulfoxides, straight chain sulfoxides or branched chain sulfoxides.

4. The oxidation reaction process according to claim 1, characterized in that the reaction medium used includes alcohol solvent selected from the group consisting of methanol, ethanol, n-propyl alcohol, isopropyl alcohol, tertiary butyl alcohol, secondary alcohol with branch and dihydroterpineol; paraffinic solvent selected from the group consisting of $C_5$–$C_{18}$ straight chain alkane, branched chain alkane, and cycloalkane; aromatic solvent selected from the group consisting of benzene, toluene, ethyl benzene, xylene, trimethyl benzene and other monosubstituted or polysubstituted alkyl benzene; ester solvent selected from the group consisting of esters of aliphatic acids, esters of aromatic acids, and trimethyl phosphate, triethyl phosphate, tripropyl phosphate, tributyl phosphate, trioctyl phosphate and other trialkyl phosphate; ether solvent selected from the group consisting of alkyl ethers, aryl ethers or aryl alkyl ethers; ketone solvent selected from the group consisting of dialkyl ketones, aryl alkyl ketones; nitrile solvent selected from the group consisting of acetonitrile, benzyl nitrile; and halogenated hydrocarbon solvent selected from the group consisting of halogenated alkanes and halogenated aromatic hydrocarbons, and these solvents can be used alone or in a combination.

5. The oxidation reaction process according to claim 1, characterized in that the oxygen source used is hydrogen peroxide ($H_2O_2$) or alkyl hydroperoxide (ROOH).

6. The oxidation reaction process according to claim 5, characterized in that the hydrogen peroxide used is 5% to 90% aqueous solution of hydrogen peroxide; and the alkyl hydroperoxide used is tertiary butyl hydroperoxide, ethylphenyl hydroperoxide, cumenyl hydroperoxide or cyclohexyl hydroperoxide.

7. The oxidation reaction process according to claim 1, characterized in that the oxygen source used is hydrogen peroxide formed in-situ from substituted hydroquinone, after the completion of the reaction and separation of the catalyst, product and unreacted raw materials, the substituted hydroquinone is regenerated by reacting substituted quinone with hydrogen under the action of hydrogenation catalyst of transition metal.

8. The oxidation reaction process according to claim 7, characterized in that the substituted hydroquinone used has the following general structure:

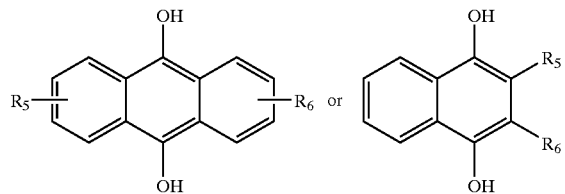

wherein $R_5$ and $R_6$ are H or $C_1$–$C_{10}$ alkyl group, and it is also possible to use a mixture of two or more said substituted hydroquinones to generate hydrogen peroxide in-situ.

9. The oxidation reaction process according to claim 8, characterized in that the transition metal hydrogenating catalyst used is those containing palladium, platinum, chromium, rhodium, nickel or ruthenium.

10. The oxidation reaction process according to claim 2, characterized in that said catalyst is heteropolyacid compounds with formula of $[R_1R_2R_3R_4N]_xH_y[A]$, wherein $R_1$, $R_2$, $R_3$, and $R_4$ are $C_1$–$C_{20}$ linear or branched alkyl, cycloalkyl, or benzyl, or $R_1R_2R_3N$ is pyridine or its homologues; A is a heteropolyanion group of P or As containing metal atom of Mo, W or V; x is an integer of from 1 to 9, and y is an integer of from 0 to 8.

11. The oxidation reaction process according to claim 2, characterized in that said catalyst is a complex represented by the general formula of $Q_mMO_3(L)$, wherein M is the central metal atom selected from the group consisting of Mo and W atom; Q is the cation moiety of formula $[R_1R_2R_3R_4N^+]$, in which $R_1$, $R_2$, $R_3$, and $R_4$ are $C_1$–$C_{20}$ linear or branched alkyl, cycloalkyl, or benzyl, or $R_1R_2R_3N$ is pyridine or its homologues; and L is a bidentate ligand containing N or O; when L is N, N-bidentate ligand, it includes $R_1$, $R_2$-2,2-dipyridine, wherein ($R_1$ and $R_2$ are substituents independently selected from the group consisting of H—, $C_1$–$C_{20}$ linear or branched alkyl group, cycloalkyl group, and aryl group at the position of 2 to 9, $R_1$, $R_2$, $R_3$-o-phenanthroline, wherein $R_1$, $R_2$, and $R_3$ are substituents independently selected from the group consisting of H—, $C_1$–$C_{20}$ linear or branched alkyl group, cycloalkyl group, and aryl group at the position of 2 to 9, m=0; when L is N, O-bidentate ligand, it includes 8-hydroxy quinoline, 2-carboxy pyridine, Schiff base formed from salicylaldehyde or substituted salicylaldehyde with primary amine and the like, m=1; when L is O, O-bidentate ligand, it includes β-carbonyl ketone or ester, m=1.

12. The oxidation reaction process according to claim 10, characterized in that said process is catalytic epoxidizing reaction process of cyclohexene for the preparation of epoxy cyclohexane, wherein the catalyst is used as reaction controlled phase-transfer catalyst, aqueous solution of hydrogen peroxide or in-situ formed hydrogen peroxide is used as oxygen source, and in organic solvent and in the presence of the catalyst, cyclohexene is selectively converted into epoxy cyclohexane through catalytic epoxidation at a temperature of from 30° C. to 100° C.

13. The oxidation reaction process according to claim 11, characterized in that said process is catalytic epoxidizing reaction process of cyclohexene for the preparation of epoxy cyclohexane, wherein the catalyst is used as reaction controlled phase-transfer catalyst, aqueous solution of hydrogen peroxide or in-situ formed hydrogen peroxide is used as oxygen source, and in organic solvent and in the presence of the catalyst, cyclohexene is selectively converted into epoxy cyclohexane through catalytic epoxidation at a temperature of from 30° C. to 100° C.

14. The oxidation reaction process according to claim 10, characterized in that said process is catalytic epoxidizing reaction process of propylene for the preparation of epoxy propane, wherein the catalyst is used as reaction controlled phase-transfer catalyst, aqueous solution of hydrogen peroxide or in-situ formed hydrogen peroxide is used as oxygen source, and in organic solvent and in the presence of the catalyst, propylene is selectively converted into epoxy propane through catalytic epoxidation at a temperature of from 30° C. to 100° C.

15. The oxidation reaction process according to claim 11, characterized in that said process is catalytic epoxidizing reaction process of propylene for the preparation of epoxy propane, wherein the catalyst is used as reaction controlled phase-transfer catalyst, aqueous solution of hydrogen peroxide or in-situ formed hydrogen peroxide is used as oxygen source, and in organic solvent and in the presence of the catalyst, propylene is selectively converted into epoxy propane through catalytic epoxidation at a temperature of from 30° C. to 100° C.

\* \* \* \* \*